(12) United States Patent
Hunter et al.

(10) Patent No.: US 6,461,585 B1
(45) Date of Patent: Oct. 8, 2002

(54) PREPARATION OF RADIOLABELLED HALOAROMATICS VIA POLYMER-BOUND INTERMEDIATES

(75) Inventors: Duncan H. Hunter, London (CA); Xizhen Zhu, Cary, NC (US)

(73) Assignee: The University of Western Ontario (CA)

( * ) Notice: Subject to any disclaimer, the term of this patent is extended or adjusted under 35 U.S.C. 154(b) by 0 days.

(21) Appl. No.: 09/529,017

(22) PCT Filed: Oct. 2, 1998

(86) PCT No.: PCT/CA98/00933

§ 371 (c)(1),
(2), (4) Date: Jul. 18, 2000

(87) PCT Pub. No.: WO99/18053

PCT Pub. Date: Apr. 15, 1999

Related U.S. Application Data

(60) Provisional application No. 60/060,886, filed on Oct. 2, 1998.

(51) Int. Cl.[7] .................... A61K 51/00; A61M 36/14
(52) U.S. Cl. ................... 424/1.85; 424/1.11; 424/1.65; 424/1.81; 424/1.89
(58) Field of Search ................ 424/1.11, 1.65, 424/1.81, 1.85, 1.89, 9.1; 206/223, 569, 570

(56) References Cited

U.S. PATENT DOCUMENTS 5,565,185 A * 10/1996 Hunter et al. ............... 424/1.85

FOREIGN PATENT DOCUMENTS

EP 693467 * 1/1996

OTHER PUBLICATIONS

Wafelman et al, 1994, Appl. Radiat. Isot., vol. 45, No. 10, pp. 997–1007.*
Vaidyanathan et al, 1993, Appl. Radiat. Isot., vol. 44, No. 3, pp. 621–628.*
Culbert et al, 1993, Reactive Polymers, vol. 19, pp. 247–253.*

* cited by examiner

Primary Examiner—Dameron L. Jones
(74) Attorney, Agent, or Firm—Barry J. Marenberg; Ivor R. Elrifi; Mintz, Levin, Cohn, Ferris, Glovsky and Popeo, P.C.

(57) ABSTRACT

According to a first aspect of the invention, a process is disclosed for the preparation of radiolabelled haloaromatic compounds. According to a second aspect of the invention, intermediate precursor insoluble polymer compounds used in the preparation of the radiolabelled haloaromatic are disclosed, as well as processes for the preparation of the intermediate precursor insoluble polymer compounds.

9 Claims, 2 Drawing Sheets

PREPARATION OF RADIOLABELLED HALOAROMATICS VIA POLYMER-BOUND INTERMEDIATES

This application is a 371 of Application No. PCT/CA98/00933, filed Oct. 2, 1998. Also, this application is based on U.S. provisional patent application No. 60/060,886, filed Oct. 2, 1998.

TECHNICAL FIELD

This invention relates to the preparation of a radiopharmaceutical. In particular, this invention relates to a process for the preparation a radiolabelled haloaromatic, as well as intermediate precursor compounds used in the process.

BACKGROUND ART

A number of radiolabelled haloaromatic compounds have found application in nuclear medicine. For example, meta-iodobenzylguanidine ("MIBG"), when radiolabelled with the iodine atom, is used in nuclear medicine as either an imaging agent for diagnosis, or as a therapeutic agent for neural crest tumors such as neuroblastoma. When labelled with the shorter-lived iodine-123, [$^{123}$I]MIBG provides diagnostic cardiac images as well as images of tumors. The longer-lived [$^{131}$I]MIBG is used at much higher radiation and chemical doses for the treatment of tumors.

By far the most common method of producing either [$^{123}$I]MIBG or [$^{131}$I]MIBG is by a Cu+ catalyzed isotopic exchange process which commences with 1–2 mg of MIBG and the desired amount of radioiodide. Because isotopic exchange is an equilibrium process, the product obtained by this process necessarily contains a significant amount of carrier MIBG. Considerable effort[1] has been placed towards developing a convenient procedure that proceeds in near quantitative radiochemical yields. However, this method has the drawback of producing [$^{131}$I]MIBG of low specific activity resulting in chemical doses of 1–5 mg when therapeutic samples are prepared. Doses of this magnitude carry potential hypertensive side effects Accordingly, routes to no-carrier-added [$^{131}$I]MIBG have been developed which could reduce the chemical dose of MIBG by about a factor of 100. Precursors to no-carrier-added [$^{131}$I]MIBG, such as 3-tributylstannylbenzylamine[2], 3-trimethylsilylbenzylguanidine[2], and 3-trimethylstannylguanidinium[3], have not found widespread application. These compounds have a short shelf life, and must be stored in a freezer shielded from light.

U.S. Pat. No. 5,555,185 discloses a no-carrier-added process of radiolabelling MIBG by halodestannylation. However, the process is disadvantageous in that a number of impurities remain in solution with the radiolabelled MIBG. In particular, toxic tin by-products remain in solution and must be separated before the radiolabelled MIBG is ready for use.

Accordingly, there is a need for a process for no-carrier-added synthesis of radiolabelled haloaromatic compounds, which can be easily and practically separated from possibly toxic impurities.

DISCLOSURE OF INVENTION

It is an object of the invention to provide a process for no-carrier-added synthesis of radiolabelled haloaromatic compounds, where the impurities can be removed by simple filtration, thereby making the process suitable for "kit" formulation.

It is also an object of the invention to provide intermediate insoluble polymer precursors which have a long shelf life and can be stored at room temperature without special conditions, and to which the unlabelled compounds and side products are bound, thereby facilitating removal of these undesirable impurities by filtration.

According to a first aspect of the present invention, a process of preparing a radiolabelled haloaromatic compound (I) of the formula:

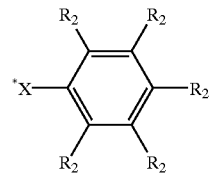

is provided, wherein:

$R_2$ is selected from an alkyl group, an aryl group, a hydrogen atom, a halogen atom, a substituted oxygen atom, a substituted nitrogen atom, a substituted sulfur atom, a carbonyl group, a cyano group, an amino group, and a guanidine group. *X is selected from any suitable radiohalide, and is preferably selected from formula:

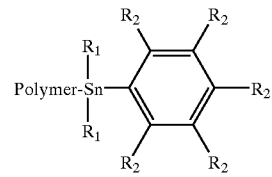

wherein $R_1$ is an alkyl group, and is preferably a butyl group. $R_2$ is as described above.

According to a third aspect of the invention, a process of preparing an intermediate insoluble polymer of the compound of formula:

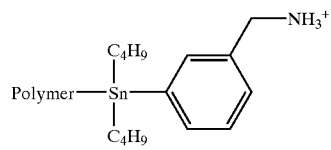

is provided. The process comprises reacting the compound of formula:

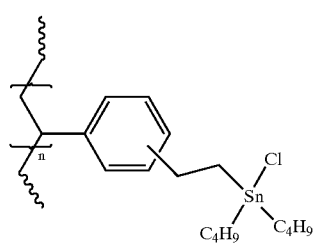

with a 1-(3-bromobenzyl)-2,2,5,5-tetramethyl-1,2,5-azadisilolidine compound of the structural formula:

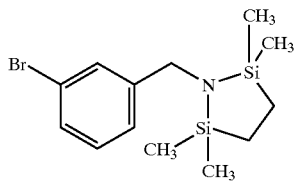

According to a fourth aspect of the invention, a process is provided for preparing an intermediate insoluble polymer compound of formula:

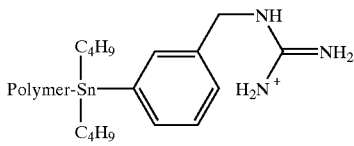

comprising the steps of:
(a) reacting a first insoluble polymer compound of formula:

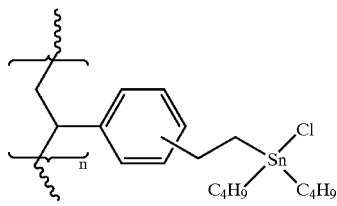

with a 1-(3-bromobenzyl)-2,2,5,5-tetramethyl-1,2,5-azadisilolidine compound of the structural formula:

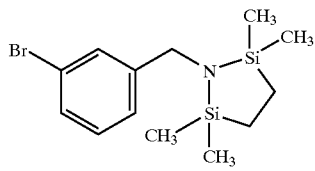

to produce the compound having the formula:

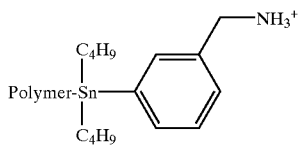

(b) reacting a compound having the formula:

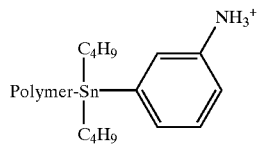

with toluene and $NCNH_2$ to convert the ammonium group to a guanidinium group.

According to a fifth aspect of the invention, a process is provided for preparing a compound of the formula:

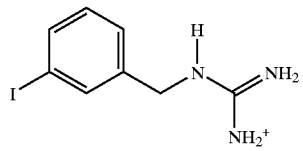

comprising contacting a compound of the formula:

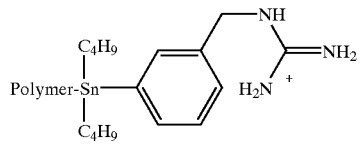

with iodine in an organic solvent.

According to a sixth aspect of the invention, a process is provided for preparing a compound of the formula:

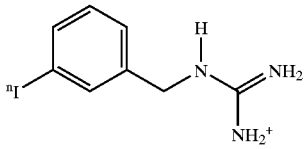

wherein n is selected from 123, 125, and 131: the process comprising contacting a compound having the formula:

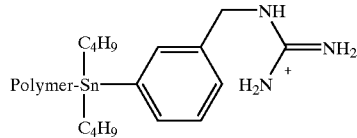

with a solution of $Na^nI$ and an oxidizing agent in the presence of a buffering agent; wherein n is as described above.

Further features of the invention will be described or will become apparent in the course of the following detailed description.

BRIEF DESCRIPTION OF THE DRAWINGS

In order that the invention may be more clearly understood, the preferred embodiment thereof will now be described in detail by way of example, with reference to the accompanying drawings, in which.

BEST MODE FOR CARRYING OUT THE INVENTION

Figure 1A:
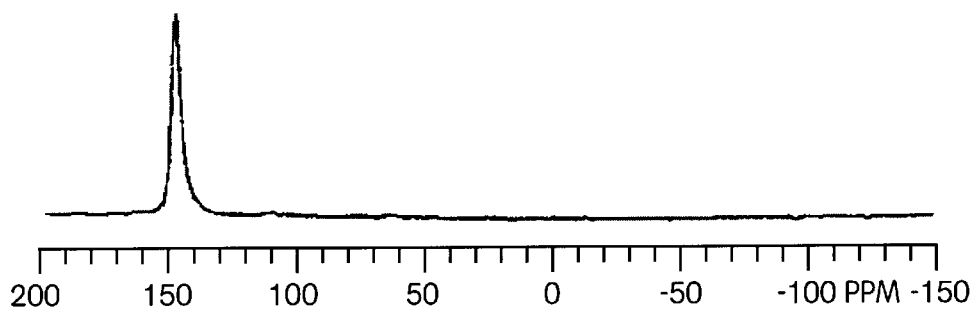
FIG. 1A shows the $^{119}Sn$ MAS NMR spectrum for Polymer 1.

The process, according to the present invention, provides for the radiohalogenation of a haloaromatic compound using a polymer-supported pharmaccutical, as follows:

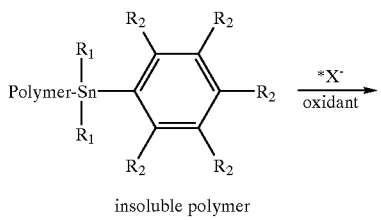

insoluble polymer

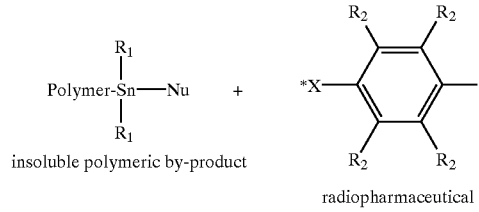

insoluble polymeric by-product     radiopharmaceutical wherein:

R$_1$ is an alkyl group, and is preferably a butyl group,;

R$_2$ is selected from an alkyl group, an aryl group, a hydrogen atom, a halogen atom, a substituted oxygen atom, a substituted nitrogen atom, a substituted sulfur atom, a carbonyl group, a cyano group, an amino group, a guanidino group;

Nu is a nucleophile provided by the solvent or oxidant; and

*X is selected from any suitable radiohalide, such as, for example, $^{131}$I or $^{123}$I.

Although the preferred embodiment of the present invention refers to isotopes of Iodine only, such references are intended by way of example, and are not intended to be limiting. The present invention may be applied to any suitable radiohalide.

According to a preferred embodiment of the present invention, a process is provided to synthesize no-carrier-added [$^{131}$I]MIBG or [$^{123}$I]MIBG using polymer-supported radiopharmaceutical precursors[4]. An insoluble polymer is prepared in which the pharmaceutical to be radiohalogenated is bound to the polymer through a tin-aryl bond as illustrated above. Treatment with the radiohalide and an appropriate oxidant results in the release of the radiohalogenated pharmaceutical while unreacted polymer and polymer side-products remain insoluble and easily removed by filtration.

The polymer above is derived by reaction of the appropriate organolithium with a polymeric chlorostannane. Polymer 1, described in detail below, is used as an intermediate compound to derive the polymer to be used in the radiohalogenation of a haloaromatic compound. Polymer 2 is one such reagent derived from Polymer 1, and Polymer 3 is the preferred polymer-supported 3-benzylguanidinium reagent for the preparation of no-carrier-added [$^{131}$I]MIBG or [$^{123}$I]MIBG. Polymers 2 and 3 are also described in detail below.

Preparation of Poly-3- and -4-(2-dibutylchlorostannyl ethyl)styrene: Polymer 1

Polymer 1 has the following structural formula:

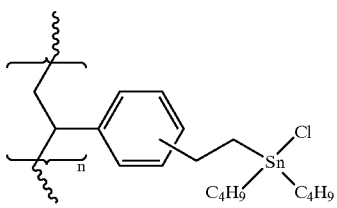

and was prepared by a known procedure[5], as shown schematically below.

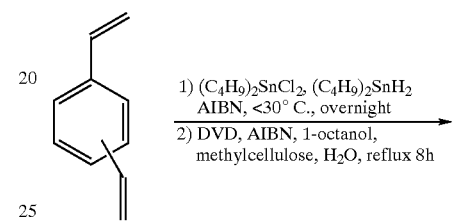

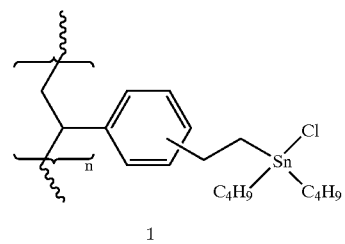

1

After being run through a short silica column to remove antioxidant, commercial divinylbenzene (36 g, 225 mmol) and di-n-butyldichlorostannane (35 g, 115 mmol) were reacted overnight under nitrogen with dibutylstannane (27.5 g, 115 mmol) in the presence of AIBN (0.75 g, 4.6 mmol) near or below 30° C. Then divinylbenzene (6.5 g, 40.6 mmol), AIBN (1.25 g, 7.6 mmol), 1-octanol (85.5 g) and methyl-cellulose (0.63 g) dissolved in water (250 mL) were added to the previously prepared monomer. This mixture was refluxed for 8 h in a resin kettle under nitrogen with rapid stirring (1000 rpm).

After cooling, water was added to the resin kettle and the solution was decanted from the granular polymer particles. Washing with water was continued until the supernatant ran clear. After a similar treatment with acetone (5×200 mL), the polymer was filtered with a coarse sintered-glass funnel and washed with methanol (2×200 mL), toluene (3×200 mL) and THF (3×200 mL). After drying overnight under vacuum at room temperature, 66.5 g (73% yield by weight) of white grainy solid was obtained.

The characteristics of Polymer 1 are preferably as follows:

Solid-state MAS $^{13}$C NMR (swollen with CHCl$_3$), δ ppm: 14.6 (CH$_3$), 18.6 (Sn—CH$_2$—), 27.7 (—CH$_2$CH$_2$CH$_3$), 28.6 (—CH$_2$CH$_3$), 42 (broad, Ar—CH—, Ar—CH$_2$— and backbone —CH$_2$—), 128 (broad, aryl CH), 144 (broad, Aryl C).

Solid-state MAS $^{119}$Sn NMR (swollen with CHCl$_3$), δ ppm.: 148.

DRIFT spectrum, cm$^{-1}$: 3036, 3060 (aromatic C—H); 2968, 2938, 2879, 2860 (aliphatic C—H): 1604, 1510 (aromatic C=C vibrations), 1486, 1450, 2968, 2938, 2879, 2860 (aliphatic C—H); 1604, 1510 (aromatic C═C vibrations), 1486, 1450.

Samples of Polymer 1 were prepared as indicated above. Polymer 1 was characterized both chemically and spectroscopically. The availability of Sn—Cl bonds was assessed by treatment of Polymer 1 with KOH in ethanol/THF at room temperature. Polymer 1 (201 mg) was soaked in 7 mL of absolute ethanol, 3 mL (3 mmol) of 1 M potassium hydroxide, and 1 mL of tetrahydrofuran for 24 h at room temperature. The polymer was filtered and washed with 70% ethanol (5×5 mL). The ethanol and THF in the filtrate were removed on rotary evaporator and the residual liquid was transferred into a 50 mL volumetric flask and topped up to the mark with water. Then 20 mL of this solution was diluted to 50 mL Erlenmeyer by addition of 1 M nitric acid. This solution was then titrated for Cl following the Mohr procedure.[6]

The amount of chloride ion released was found to be 1.7±0.1 mmol/g of polymer. If the polymer was composed exclusively of the units indicated in the structure shown for Polymer 1, the maximum amount of chloride released would be 2.5 mmol/g of polymer. However, significant amounts of divinylbenzene had been used when forming the polymer and the yield of material was 32%.

Figure 1B:
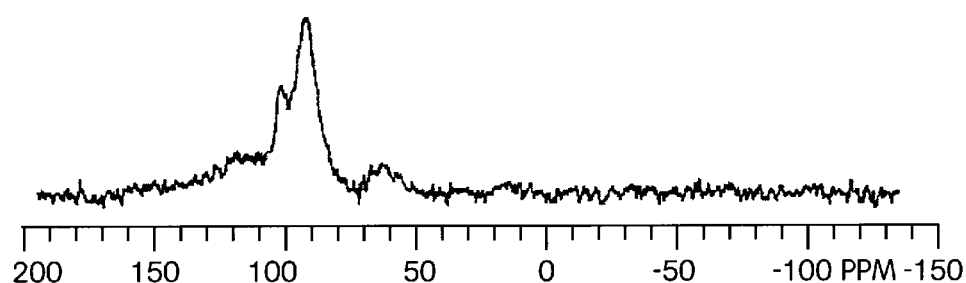
FIG. 1B shows the $^{119}Sn$ MAS NMR spectrum for Polymer 1 after hydrolysis.

Polymer 1 was also investigated by MAS NMR spectroscopy on samples that had been preswollen with chloroform which had the effect of sharpening the signals. The $^{13}$C NMR spectrum was consistent with the anticipated structure showing signals for all of the carbons. The signals for the backbone CH and $CH_2$ and phenyl carbons were quite broad and indistinct. However, the $CH_2$—$CH_2$ carbons and the carbons on the butyl chains were readily assigned by analogy with non-polymeric species. The $^{119}$Sn NMR spectrum (FIG. 1A) showed but one peak at 148 ppm consistent with species of the general structure $R_3$Sn—Cl. This confirmed that all of the tin atoms were bonded to chlorine in spite of the apparent discrepancy in the hydrolysis results mentioned above. This was particularly reassuring since IR spectra invariably gave a broad absorption near 3500 $cm^{-1}$ which was consistent with hydrolysis of the Sn—Cl bond to Sn—OH. The $^{119}$Sn NMR spectrum of hydrolysed material (FIG. 1B) was obtained and showed the complete absence of the peak at 148 ppm with a group of peaks appearing at about 90 ppm which confirmed that Polymer 1 has tin bonded exclusively to chlorine and that all of these bonds are available for hydrolysis.

As illustrated in detail below. Polymer 1 was preferably converted in two steps first into Polymer 2 which bears the 3-benzylammonium moiety and then into Polymer 3 functionalised with a 3-benzylguanidinium species.

Preparation of polymer-supported 3-benzylammonium chloride: Polymer 2

Preparation of 1-(3-bromobenzyl)-2,2,5,5-tetramethyl-1,2,5-azadisilolidine: Compound 4

The conversion of Polymer 1 into Polymer 2 was preceded by the preparation of 1-(3-bromobenzyl)-2,2,5,5-tetramethyl-1,2,5-azadisilolidine. 3-Bromobenzylamine hydrochloride (25.0 g, 112.3 mmol) was converted to the free base by neutralization with sodium hydroxide and extraction into methylene chloride. Drying and solvent removal resulted in 20.3 g of a brown liquid which was used as such. To the above 3-bromobenzylamine (20.3 g, 109 mmol), in a round bottom flask equipped with a condenser and under argon atmosphere, was added 150 mL of methylene chloride and 30.3 mL (217 mmol) of triethylamine. To this stirred mixture cooled with an ice bath was added slowly 109 mL (109 mmol) of 1 M 1,2-bis(chlorodimethylsilyl) ethane dissolved in methylene chloride. During the addition, considerable precipitate formed. The ice-bath was removed and the mixture was stirred for another 6.5 h at room temperature. The white solid was removed by filtration and washed with methylene chloride (2×30 mL). The filtrate was evaporated using a rotary evaporator resulting in further precipitate formation. Hexanes (100 mL) were added to this mixture. The solid was removed by filtration and washed with hexanes (2×20 mL). After hexane removal from the filtrate, a yellowish liquid was obtained which was distilled to yield 29.0 g (82% yield) of light yellowish liquid (bp. 93–5° C./0.05 mm Hg).

Compound 4 preferably had the following characteristics:

$^1$H NMR spectrum δ (acetone-d6): δ0 (s, 12H, $CH_3$); 0.79 (s, 4H, Si—$CH_2$—$CH_2$—Si); 4.05(s, 2H, Ar—$\underline{CH}_2$—N); 7.25 (t, 1H, 5-H), 7.30 (d, 1H, 6-H), 7.38 (d, 1H, 4-H), 7.47 (s, 1H, 2-H).

$^{13}$C NMR spectrum (chloroform-d): δ0 (CH3); 8.2 (Si—$CH_2$—$CH_2$—Si); 45.8 (Ar—$CH_2$—N); 122.4 (C-3), 125.3 (C-6), 129.5 (C-5), 129.7 (C-2),130.9 (C-4), 146.2 (C-1). IR (neat); $cm^{-1}$ 3068 (aromatic C—H stretch); 2949, 2903, 2857 (aliphatic C—H stretch); 1604, 1484 (aromatic C═C vibrations); 849 (vs asymmetric (Si—N—Si stretching), 784(pCH3), 678 ($v_{sa}$Si—C). (aromatic C—H bending). MS: M/Z 329, 327, 314, 312, 169, 130, 116, 100, 90, 73, 59, 45. Anal. required for $C_{13}H_{22}BrNSi_2$, m/e 327.0474; found, m/e 327.0479.

Following the preparation of 1-(3-bromobenzyl)-2,2,5,5-tetramethyl-1,2,5-azadisilolidine, the preparation of Polymer 2 proceeded as follows:

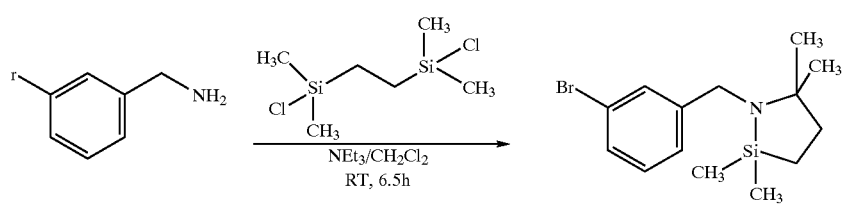

-continued

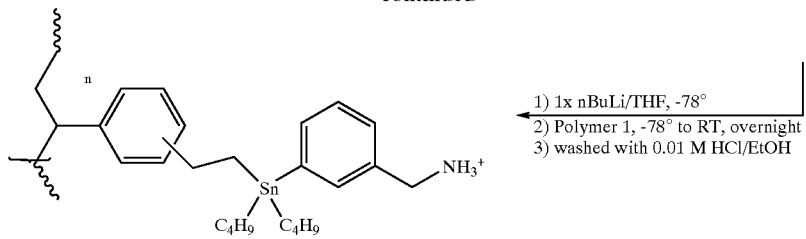

To 25.0 g (76.1 mmol) of Compound 4 in a three-neck flask equipped with an argon inlet, a serum cap and a powder addition sidearm containing Polymer 1 (28.6 g) was added 250 mL of freshly distilled dried tetrahydrofuran. To this flask cooled to −78° C. was added slowly 30.5 mL (76.1 mmol) of 2.5 M n-butyllithium. The initially colourless solution turned purple and then brownish at 25 min. Polymer 1 was then tipped into the reaction solution and the mixture was stirred gently in the dry-ice-acetone bath for 7 h. After the temperature was allowed to rise to room temperature over 2 h and then held at room temperature for another 1 h. methanol (10 mL) was added followed by sufficient 1M hydrogen chloride to give a pH of 4–5. The mixture was stirred overnight and allowed to stand stirred for 15 min.

After the upper cloudy solution was decanted, 200 mL of methanol was added. Again the cloudy upper layer was decanted and this process was repeated 4 times. The polymer was filtered through a coarse sintered glass funnel and washed with 50% methanol/water solution (100 mL), methanol (3×100 mL), and 96% ethanol (50 mL). After vacuum drying at room temperature, 30.1 g (84 wt % yield) of a white grainy material was obtained.

The characteristics of Polymer 2 were preferably as follows:

Solid-state MAS $^{13}$C NMR spectrum: δ14.6 (CH$_3$), 18.6 (Sn—CH$_2$-), 27.7 (—CH$_2$CH$_2$CH$_3$), 28.6 (—CH$_2$CH$_3$), 42 (broad, Ar—CH—, Ar—CH$_2$— and backbone —CH$_2$-), 128 (broad, aryl CH), 144 (broad, Aryl C)

Solid-state MAS 119Sn NMR spectrum; δ−43.6 ppm

IR spectrum (KBr): cm$^{-1}$ 3435 (broad, —NH$_3^-$ stretches); 3027(aromatic C—H stretch); 2927, 2857 (aliphatic C—H stretches); 1611, 1498 (aromatic C═C vibrations).

Because 3-bromobenzyl amine has reactive NH bonds, the amino group was first protected as an azadisilolidine[7] and then reacted with one equivalent of n-butyllithium. Polymer 1 was added to the presumed monolithium species so prepared. Polymer 2 was characterized by $^{13}$C and $^{119}$Sn MAS NMR spectroscopy.

Figure 1C:
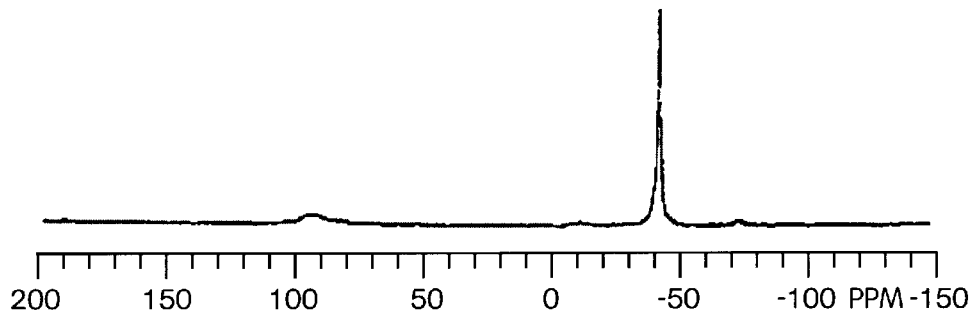
FIG. 1C shows the $^{119}Sn$ MAS NMR spectrum for Polymer 2.

The $^{13}$C NMR spectrum was consistent with the proposed structure. Again, the signals attributed to the backbone CH and CH$_2$ carbons and the phenyl carbons appeared as broad peaks. The peaks due to the Sn—CH$_2$—CH$_2$ carbon was identifiable as well as the carbons of the n-butyl group. The benzylic carbons were not readily identified. Perhaps most characteristic was the shift in the Sn—CH$_2$—C$_3$H$_7$ carbon signals from 18.6 ppm for Polymer 1 to 10.5 ppm for Polymer 2. Again the IR spectrum gave a broad absorption near 3500 cm$^{-1}$ indicating that considerable hydrolysis accompanied this reaction. However as indicated in FIG. 1C, the $^{119}$Sn spectrum showed primarily one peak at −43.6 ppm with a small peak at 90 ppm consistent with SnOH and representing about 10% of the tin signals. Thus it would seem that all of the Sn—Cl bonds had reacted with the organolithium reagent with a small amount of concurrent hydrolysis.

Iodination of Polymer 2

The iodination of Polymer 2 proceeded in accordance with the following reaction:

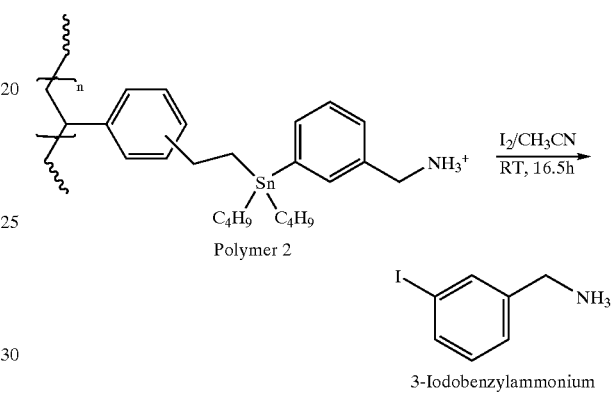

Polymer 2

3-Iodobenzylammonium

To the previously prepared Polymer 2 (100 mg) was added 10 mL of methanol and 1 mL of 0.2 M iodine in acetonitrile solution. After stirring gently at room temperature for 16.5 h, 1 mL of 1.0 M sodium metabisulphite solution was added. The mixture was transferred into a 100 mL volumetric flask and topped up to 100 mL with 0.01 M KH$_2$PO$_4$. An aliquot was filtered through a syringe filter, and the filtrate was analyzed by HPLC . The retention time of 3-iodobenzylammonium peak was 8.8 min and the amount was determined by comparison to a standard 3-iodobenzylammonium hydrochloride solution (0.4 mM).

Figure 1D:
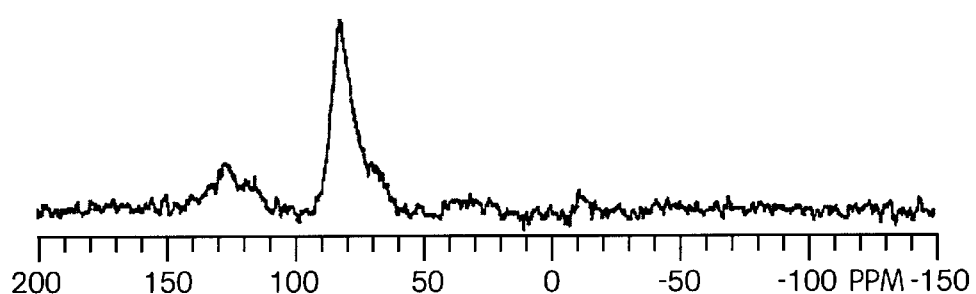
FIG. 1D shows the $^{119}Sn$ MAS NMR spectra for Polymer 3 recovered after iodination.

The extent of reaction in forming Polymer 2 and the availability of the 3-benzyl ammonium species in Polymer 2 was probed by reaction with iodine as illustrated above. This was anticipated to yield the 3-indobenzyl ammonium ion ("MIBA") which was identified and quantified by HPLC. It was found that about 0.95±0.05 mmol/g of 3-iodobenzyl ammonium ion was released per gram of Polymer 2. Again this was somewhat less that the maximum calculated amount if Polymer 2 had the structure indicated above. However, $^{119}$Sn NMR spectroscopy proved to be of considerable value as shown in FIG. 1D. A comparison of FIG. 1C for Polymer 2 and FIG. 1D for polymer 2 recovered after iodination shows a complete loss of the signal at −43.6 ppm consistent with complete release of the 3-benzyl ammonium group.

Preparation of polymer-supported 3-benzylguanidinium chloride: Polymer 3

Preferably, the synthesis of Polymer 3 involved treatment of Polymer 2 with a large excess of cyanamide to convert the ammonium group into a guanidinium group, as illustrated below.

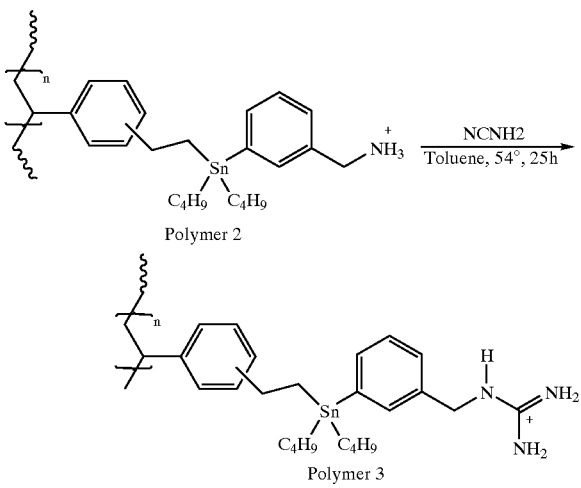

Polymer 2

Polymer 3

Under an argon atmosphere, 20.0 g of Polymer 2, 15.1 g (360 mmol) of cyanamide, 100 μL (0.72 mmol) of triethylamine and 250 mL of toluene were added to a flask equipped with a reflux condenser. The mixture was heated for 25 h at 54° C. and the hot reaction mixture was filtered through a coarse sintered glass funnel. The polymer was washed with acetonitrile (4×100 mL), methanol (4×100 mL) and acetonitrile (2×100 mL). After vacuum drying at room temperature overnight, 20.7 g of white grainy material was obtained.

The characteristics of Polymer 3 are preferably as follows:

IR spectrum (KBr): cm$^{-1}$ 3340, 3271, 3174 (N—H Stretch); 3066, 3027 (aromatic C—H Stretch); 2978, 2929, 2880, 2860 (aliphatic C—H stretch); 1677, 1658 (C=N stretch); 1521, 1496 (aromatic C=C vibrations); 719 (aromatic C—H bend).

Iodination of Polymer 3

The iodination of Polymer 3 proceeded in accordance with the following reaction:

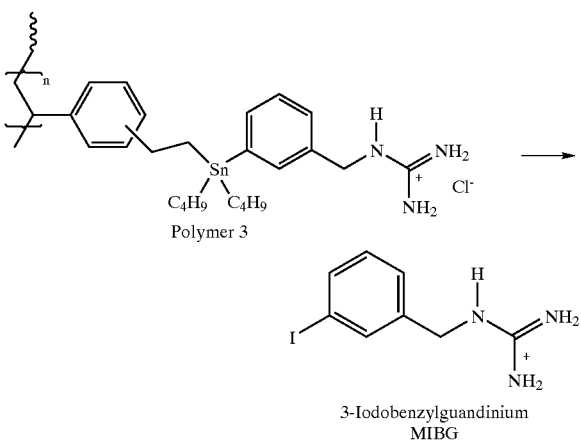

Polymer 3

3-Iodobenzylguandinium
MIBG

To 26.4 mg of Polymer 3 suspended in 4 mL of methanol was added 300 μL of 0.2 M iodine in acetonitrile solution. After stirring for 13.5 h at room temperature, 0.1 mL of 1 M sodium metabisulphite solution was added. The mixture was transferred into a 100 mL volumetric flask and topped up to 100 mL with 0.01 M KH$_2$PO$_4$ buffer. After filtering through a syringe filter, the filtrate was analysed by HPLC by comparison to standard 3-iodobenzylammonium chloride solutions (0.4 mM) and 3-iodobenzylguanidinium chlorideref solutions (0.2 mM) which had a retention times of 8.7 min and 15.6 min respectively.

Unreacted ammonium groups resulted in the release of the 3-iodobenzyl ammonium ion while ammonium groups that had reacted with cyanamide would result in the release of the 3-iodobenzylguanidinium ion, as illustrated above. Thus, at selected time intervals, polymeric material was isolated from the reaction mixture and treated with an excess of iodine. After reduction of the iodine, aliquots were analyzed by HPLC and the results are presented in FIG. 3. At 75° C. after 1 h, 80% of the ammonium groups had been converted to guanidinium groups and by 2 h conversion had progressed to 96.2%. By 5 h, there was less than 0.3% of unreacted ammonium groups.

Figure 2:
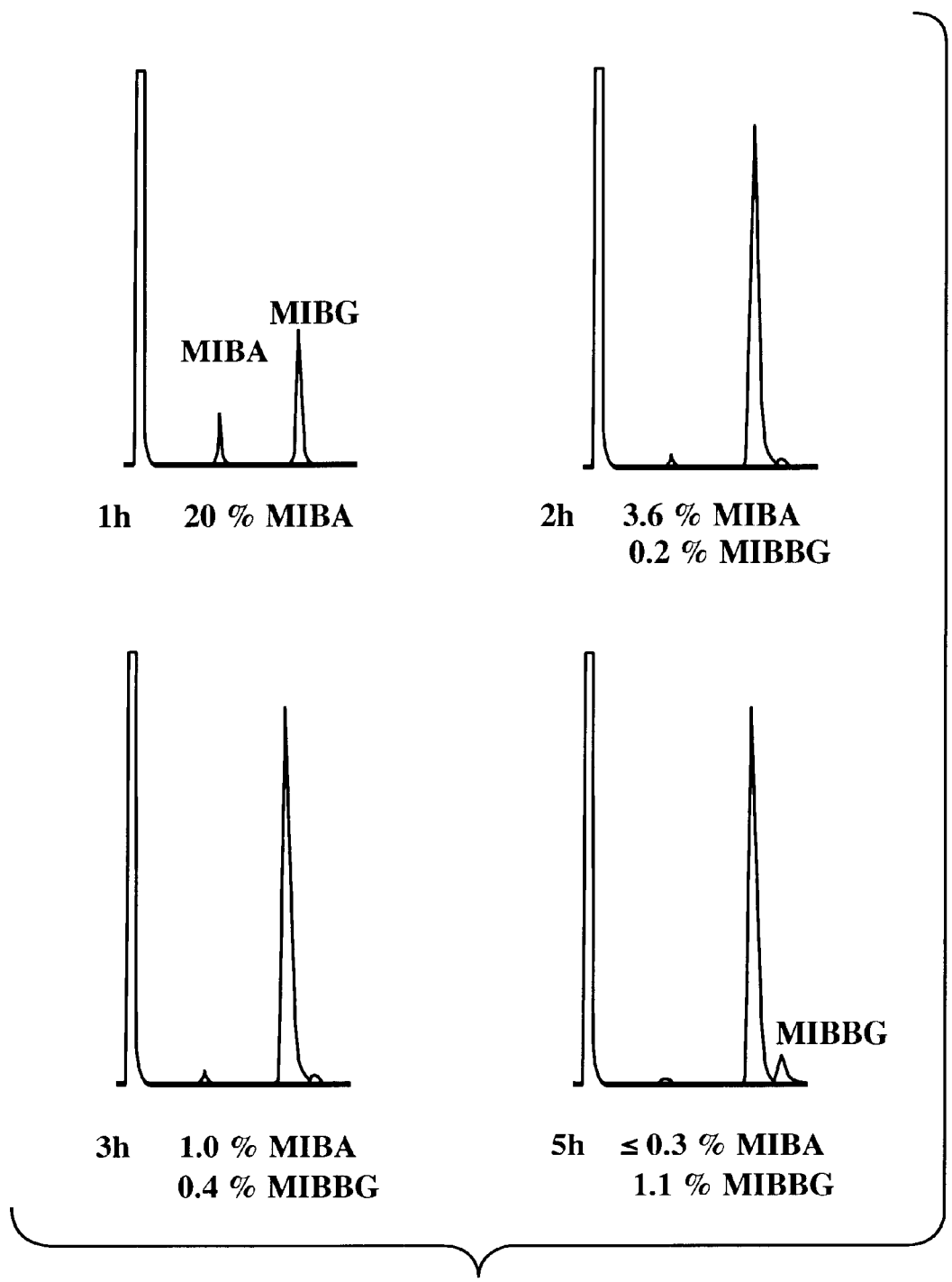
FIG. 2 shows the HPLC analysis of the iodination products of reaction of Polymer 2 with cyanamide at selected reaction times.

However, a new peak with a retention time slightly longer than the 3-iodobenzylguanidinium was observed. This material was identified to be the 3-iodobenzylblguanidinium ion in two ways. First, an authentic sample of 3-iodobenzylbiguanidinium nitrate was produced[8], as described in detail below. The sample was found to have an identical retention time with the new peak. Secondly, a small sample of the new material was isolated from a reaction that was allowed to run considerably longer and at a higher temperature than those shown in FIG. 2. Although not enough material could be isolated in a sufficiently pure form to allow a mixed mp., the $^{13}$C NMR spectrum was identical with the authentic sample of 3-iodobenzylbiguanidinium nitrate that had been produce. The guanidinium group reacted further with cyanamide, but at a rate considerably slower than the ammonium group so that the biguanidinium species does not start to appear until very late in the conversion process.

With this time course in mind, a reasonably large batch of polymer 2 was reacted for 25 h. at 54° C. After the ususal washing, Polymer 3, so produced, was analyzed by iodination to yield 3-iodobenzyl guanidinium at a level of 1.1±0.05 mmol/g of Polymer 3.

Preparation of 3-iodobenzylbiguanidinium nitrate

In a 25 mL flask, 3-iodobenzylamine hydrochloride (2.0 g, 7.4 mmol) was combined with 0.62 g (7.4 mmol) of dicyandiamide and an argon atmosphere was introduced. The mixture was melted at 154° C. for 30 min and water (20 mL) was added to dissolve the brownish solid. HPLC analysis showed 8 mol % of 3-iodobenzylamine hydrochloride, 17 mol % of MIBG and 75 mol % of 3-iodobenzylbiguanidinium nitrate (excluding dicyandiamide at 9.6 min) with a retention times of 6.1 min, 11.2 min and 12.7 min respectively. After decolorizing with charcoal, the solution was adjusted to pH~9 with saturated sodium carbonate. The upper aqueous solution was decanted from the oil which was separated. Water (5 mL) was added to the oil followed by 1 M nitric acid to a pH~5. A lot of bubbles formed during the addition of nitric acid and the mixture turned into a clear solution at pH~5. White crystals formed about 1 minute later.

After 20 min. at room temperature, the crystals were collected by filtration and washed with water (3×3 mL). After drying, 1.22 g of white crystals were obtained. Concentration of the filtrates to about 10 mL yielded 0.23 g more of white crystals. The two batches of crystals were combined and recrystallized using acetonitrile (25 mL) to provide 0.25 g of white mushroom shape crystals. HPLC analysis showed 99 mol % of 3-iodobenzylbiguanidinium nitrate, 1 mol % of MIBG and dicyandiamide. The 0.25 g of crystals were recrystallized again from 6 mL of acetonitrile to yield 99.3 mg (4% yield) of white mushroom shape crystals of mp 133.5–134.5° C.

The characteristics of the 3-iodobenzylbiguanidinium nitrate were preferably as follows:

$^1$H NMR spectrum (methanol-$d_4$): δ4.34 (d, 2H, $CH_2$), 7.05 (t, 1H, 5-H), 7.28 (d, 1H, 6-H), 7.56 (d, 1H, 4-H), 7.63 (s, 1H, 2-H).

$^{13}$C NMR spectrum (methanol-d4): δ45.5 ($CH_2$), 95.3 (C-3) 127.9 (C-6), 131.5 (C-5), 137.4 (C-2), 137.5 (C-4), 142.4 (C-2), 160.3 (middle C=N), 162.1 (terminal C=N).

FT-IR spectrum (KBr): $cm^{-1}$ 3506, 3467, 3428, 3330, 3301, 3213 (N—H stretch); 2968.1, 2938.9 (aliphatic C—H stretch); 2440 (—NH2+ stretch); 1658, 1638 (C=N stretch); 1555 (asymmetric NO3– stretch); 1428.0, 1394 (symmetric NO3– stretches); 782 (aromatic C—H bend).

UV spectrum: $δ_{max}$=232 nm, $E_{max}$=2.49×104. Anal. calc'd for C9H13IN6O3: C, 28.44; H, 3.45; N, 22.11: I, 33.38. Found; C, 28.61; H, 3.44; N, 22.07; I, 33.19.

Radioiodination of Polymer 3

Following the successful completion of the iodination of Polymer 3, the radioiodination of Polymer 3 using sodium [$^{131}$I]iodide, proceeded in accordance with the following reaction:

and a peak at 15.6 min which, by coinjection, was confirmed to be MIBG. The corresponding radioactivity trace showed a single peak at 15.6 min.

The success of the radioiodination was assessed by HPLC using both an UV detector and a γ-ray detector. The oxidant, $H_2O_2$/HOAc. or its by-products are readily separable from any [$^{131}$I]MIBG produced, and results of this oxidizing system are presented in Table 1. Labelling reactions were run at room temperature on about one or two grains of Polymer 3 in a mixture of methanol and 0.1 M $KH_2PO_4$ using Na $^{131}$I. Under these conditions after filtration, essentially all of the radioactivity was found in solution either as $^{131}$I$^{31}$ or as [$^{131}$I]MIBG as evidenced by their HPLC retention times using a radioactivity detector. Table 1 shows the effect on the radiochemical yield of [$^{131}$I]MIBG of increasing the concentration of $H_2O_2$ and acetic acid at various reaction times. As the first column indicates, the exclusion of acetic acid from the reaction mixture led to low yields and apparently slow reactions. The is third column indicates a general increase in yield with reaction time. At two hour reaction times. increasing concentrations of $H_2O_2$ and acetic acid led to increased yields which approached near quantitative conversion. It was these conditions that were chosen for preparation of [$^{131}$I]MIBG, as illustrated.

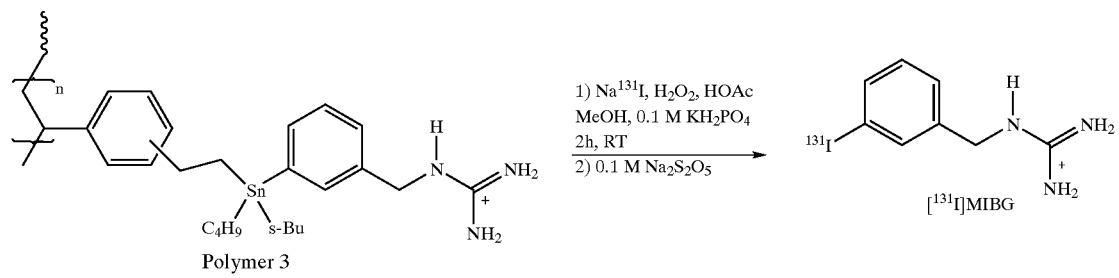

Into a 2 mL vial was placed 0.5 mg of Polymer 3, 300 μL of methanol, 100 μl of 0.1 M potassium dihydrogen orthophosphate, 45.5 MBq of a Na$^{131}$I solution and a 100 μL aliquot of a solution prepared from 2 mL of acetic acid and 2 mL of 50% hydrogen peroxide solution diluted to 50 mL with water. The mixture was occasionally shaken for 2 h at room temperature and then 200 μL of 0.1 M sodium metabisulphite was added to the reaction mixture.

After filtration through a syringe filter, the filtrate was analyzed by HPLC. The UV detector trace showed a large peak at the solvent front and several smaller peaks well before MIBG peak. The corresponding radioactivity detector trace showed two peaks at 1.9 and 15.6 min which were confirmed by coinjection to be $^{131}$I-(2.4%) and [$^{131}$I]MIBG (97.6%) respectively.

An aliquot of the reaction mixture, 25.4 MBq, was passed through a Sep-Pak™ cartridge and washed with 5 mL of water. Radioactivity was found in the washes, 1.0 MBq, and on the cartridge, 24.4 MBq. Washing of the cartridge with 1.3 mL of 42% ethanol, released 20.0 MBq of radioactivity into the washes. A wash with 1 mL of methanol released a further 3.1 MBq of [$^{131}$I]MIBG for a total of 23.1 MBq (95%). The washes were analyzed by HPLC The trace from the UV detector showed two small peaks at the solvent front

TABLE 1

Radiochemical yeild of [$^{131}$I]MIBG from treatment of Polymer 3 with NA $^{131}$I and $H_2O_2$/HOAc as oxidant as a function of reaction time and oxidant concetration

| Reation$^a$ time | [$H_2O_2$], mM/[HOAc], mM | | | | |
|---|---|---|---|---|---|
| (min) | 50/0 | 20/24 | 37/42 | 50/57 | 60/68 |
| 30 | 0 | | 30 | | |
| 60 | | 30 | 70 | 63 | |
| 120 | | 45 | 80 | 90 | 98 |
| 150 | 56 | | | | |
| 180 | | | 85 | | |

$^a$Reactions were run at room temperature in a mixture of methanol and .01M $KH_2PO_2$.

Purification of the product from the radiolabelling reaction involved two steps. The first was simple filtration through a syringe tip filter. An HPLC analysis of this product using a UV detector showed a large peak at the solvent front and several minor peaks. The radioactivity detector snowed two peaks corresponding to $^{131}$I- at about 2% and the other to [$^{131}$I]MIBG at 98%. The second step in the purification involved selective absorption and desorption of the [$^{131}$I] MIBG onto a C18 Sep-Pak™ cartridge. When the primarily aqueous solution from the filtration step was passed through the C18 Sep-Pak™ cartridge, essentially all of the radioactivity was absorbed onto the cartridge with the small amount of iodide passing through. When the cartridge was washed with ethanol/water, 82% of the radioactivity was released. A further 10% was released when methanol was used as eluant.

An HPLC analysis of these solutions, using an UV detector, showed two small peaks near the solvent front and a small peak at the retention time of MIBG. The area of this peak was rather too small to allow a reliable calculation of the specific activity of the [$^{131}$I]MIBG. The corresponding radioactivity trace showed but one peak at the retention time of MIBG. Thus following this procedure, the no-carrier-added [$^{131}$I]MIBG was produced in about 92% radiochemical yield with a specific activity of $\geq 500$ Ci/mmol.

[$^{123}$I]MIBG was produced using Iodobeads™ as the oxidant, which resulted in a radiochemical yield of about 55%. Since later experiments with Na$^{131}$I showed that about 45% of the radioactivity remained absorbed to the insoluble polymeric materials, this experiment demonstrates that Polymer 3 is an effective precursor to [$^{123}$I]MIBG. Similar result can also be expected with [$^{125}$I]MIBG.

The process, according to the present invention, produces no-carrier-added [$^{131}$I]MIBG in $\geq 90\%$ radiochemical yield and high chemical purity. Isolation and purification are simple, involving just filtration and absorption and desorption onto a C18 Sep-Pak™ cartridge. No-carrier-added material should avoid the potential pharmacological side effects accompanying the current method of production.

Although the above description refers to radioiodination of MIBG, such references are not intended to be limiting. The process and intermediate compound according to the present invention can be used for synthesis of any number radiolabelled haloaromatic compounds.

It will be appreciated that the above description relates to the preferred embodiment by way of example only. Many variations on the invention will be obvious to those knowledgeable in the field, and such obvious variations are within the scope of the invention as described and claimed, whether or not expressly described.

INDUSTRIAL APPLICABILITY

The process and precursor compounds, according to the present invention, is useful in the field of nuclear medicine for the production of radiopharmaceutical compounds.

REFERENCES

1) Wafelman, A. R. Konings, M. C. P., Hoefnagel, C. A., Maes, R. A. A. and Beijnen, J. H., *Appl Radiat. Isot.*, 997 (1994) and references therein.
2) Vaidyanathan, G. and Zalutsky, M. R., *Appl Radiat. Isot.*, 621 (1993).
3) Flanagan, R. J., Goel, A., Charleson, F. P. and Hunter, D. H., J. Label. Comp. Radiopharm., 636 (1995). Hunter, D. H., Goel, A. and Flanagan, R. J., "Process for the Preparation of Radiolaelled meta-Halobenzylguanidine". U.S. Pat. No. 5,565,185.
4) Culbert, P. A., and Hunter, D. H., Polymer Supported Radiopharmaceuticals: $^{123}$I and $^{131}$I- Labelled N-Isopropyl-4-Iodoamphetamine, *Reactive Polymers*, 19, 247–253 (1993).
5) Gerigk, U., Gerlach, M., Neumann, W. P., Veiler, R. and Weintritt, V., *Synthesis*, 448 (1990).
6) R. A. Day. Jr.: A. L. Underwood, *Quantitative Analysis Laboratory Manual* (Prentice-Hall, Inc), 2$^{nd}$ ed., p. 115–116, Englewood Cliffs, N.J., 1967.
7) Djuric, S., Venit, J., and Magnus, P., *Tetrahedron Lett.*, 22, 1787–1790 (1981).
8) Shapiro, S. L., Parino, V. A., Rogow, E., Freeman, L., *J. Am. Chem. Soc.*, 81, 3728 (1959).

What is claimed is:

1. A process of preparing a radiolabelled haloaromatic compound (I) of the formula:

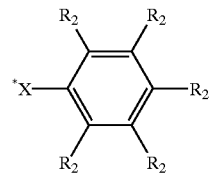

wherein:

$R_2$ is selected from an alkyl group, an aryl group, a hydrogen atom, a halogen atom, a substituted oxygen atom, a substituted nitrogen atom, a substituted sulfur atom, a carbonyl group, a cyano group, an amino group, and a guanidino group;

*X is any radiohalide;

said process comprising reacting a radiohalogen ion with a insoluble polymer compound (II) in the presence of a solvent and an oxidant, said polymer compound (II) having the formula:

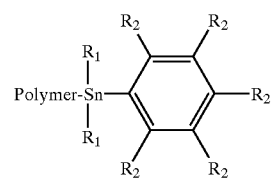

wherein, $R_1$ is an alkyl group; and $R_2$ is as described above.

2. The process of claim 1, wherein $R_1$ is a butyl group.

3. The process of claim 1 wherein *X is selected from $^{131}$I, $^{125}$I, and $^{123}$I.

4. The process of claim 1, wherein the solvent is an organic solvent.

5. The process of claim 4 where compound (I) has the formula:

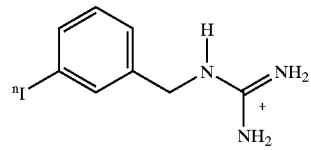

wherein n is selected from 123, 125, and 131.

6. The process of claim 5, wherein n is 123.

7. The process of claim 5, wherein n is 131.

8. The process of claim 5, wherein n is 125.

9. The process of claim 5 wherein the polymer compound (II) has the formula:

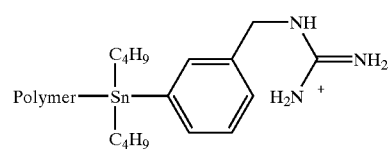

* * * * *

UNITED STATES PATENT AND TRADEMARK OFFICE
CERTIFICATE OF CORRECTION

PATENT NO. : 6,461,585 B1
DATED : October 8, 2002
INVENTOR(S) : Duncan H. Hunter and Xizhen Zhu It is certified that error appears in the above-identified patent and that said Letters Patent is hereby corrected as shown below:

Column 2,
Line 41, insert:
-- According to a second aspect of the invention, an intermediate insoluble polymer compound is provided. The compound comprises the repeating unit formula:

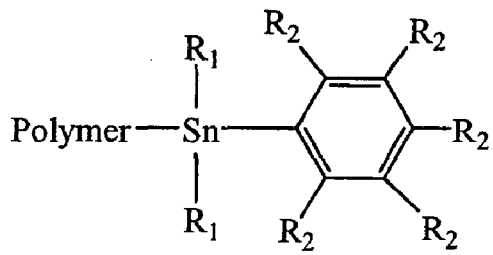

wherein, $R_1$ is selected from an alkyl group; and $R_2$ is selected from an alkyl group, an aryl group, a hydrogen atom, a halogen atom, a substituted oxygen atom, a substituted nitrogen atom, a substituted sulfur atom, a carbonyl group, a cyano group, an amino group, and a guanidino group --.

Column 7,
Line 47, delete "." after the word "below" and replace with -- , --.

Column 8,
Line 41, delete "125.3" and replace with -- 126.3 --.
Line 46, delete "($v_{sa}$ Si—C)" and replace with -- ($v_{as}$ Si—C) --.

Column 9,
Line 26, delete "stirred" and replace with -- unstirred --.
Line 32, delete "96%" and replace with -- 95% --.

Column 10,
Line 49, delete "3-indobenzyl" and replace with -- iodobenzyl --.

UNITED STATES PATENT AND TRADEMARK OFFICE
CERTIFICATE OF CORRECTION

PATENT NO. : 6,461,585 B1
DATED : October 8, 2002
INVENTOR(S) : Duncan H. Hunter and Xizhen Zhu It is certified that error appears in the above-identified patent and that said Letters Patent is hereby corrected as shown below:

<u>Column 12,</u>
Line 10, delete "3-iodobenzylblguanidinium" and replace with -- 3-iodobenzylbiguanidium --.
Line 30, delete "produce" and replace with -- produced --.
Line 36, delete "ususal" and replace with -- usual --.

<u>Column 14,</u>
Line 20, delete "is".
Line 22, delete "times." and replace with -- times, --.
Line 63, delete "snowed" and replace with -- showed --.

Signed and Sealed this

Twenty-seventh Day of May, 2003

JAMES E. ROGAN
*Director of the United States Patent and Trademark Office*